United States Patent
Ohno et al.

[19]

[11] Patent Number: 6,052,429
[45] Date of Patent: Apr. 18, 2000

[54] X-RAY ANALYZING APPARATUS

[75] Inventors: Kazunaga Ohno; Yukio Hashizume, both of Musashino; Masahiko Kuwata, Akishima; Toshiyoshi Watanabe, Akishima; Hiroshi Ohkubo, Akishima, all of Japan

[73] Assignees: DKK Corporation; Jeol Ltd., both of Tokyo, Japan

[21] Appl. No.: 09/026,496

[22] Filed: Feb. 19, 1998

[30] Foreign Application Priority Data

Feb. 20, 1997 [JP] Japan .................................. 9-035972
Aug. 18, 1997 [JP] Japan .................................. 9-235490

[51] Int. Cl.[7] .................................................. G01N 23/223
[52] U.S. Cl. ............................................ 378/45; 378/161
[58] Field of Search ................................. 378/45, 44, 47, 378/161, 140

[56] References Cited

U.S. PATENT DOCUMENTS

| | | | |
|---|---|---|---|
| 2,665,391 | 1/1954 | Bleeksma | 378/161 |
| 3,296,478 | 1/1967 | Ichinokawa | 378/161 |
| 5,226,067 | 7/1993 | Allred et al. | 378/161 |
| 5,740,223 | 4/1998 | Ozawa et al. | 378/161 |

FOREIGN PATENT DOCUMENTS

| | | |
|---|---|---|
| 1140100 | 6/1989 | Japan . |
| 2253598 | 10/1990 | Japan . |

OTHER PUBLICATIONS

"X-ray Energy Spectrometry," Rolf Woldseth, Chapters 3,4, Quantitative Analysis p. 3.20, Jun. 1973.

*Primary Examiner*—David P. Porta
*Attorney, Agent, or Firm*—Friedman Siegelbaum, LLP

[57] ABSTRACT

An X-ray analyzing apparatus according to the invention includes an excitation ray generator for applying an excitation ray onto a sample, and an X-ray detector which is sealed in a vacuum container along with a cooling device; a first X-ray passing layer, where a first gas exists, is provided in a path through which the characteristic X-ray generated from the sample travels to the X-ray detector; X-ray transmission windows are provided on the first X-ray passing layer and on the vacuum container so as that the characteristic X-ray can reach to the X-ray detector through the windows; the first and second X-ray transmission windows are separated from each other so as to provide a second X-ray passing layer therebetween; and the second X-ray passing layer is arranged to be a vacuum or a second gas is circulated through the second X-ray passing layer. According to this construction, it can be prevented that the first gas breaks into the vacuum container in which the X-ray detector is sealed; thus the deterioration of the cooling efficiency caused in that the vacuum condition in the vacuum container is decreasing prevented, so that the consuming amount of the cooling medium for use in cooling the X-ray detector can be reduced.

9 Claims, 5 Drawing Sheets

Variation in consumption rate of liquid nitrogen per day

Sample graph of sulfur concentration
measured using an X-ray analyzing apparatus

X-RAY ANALYZING APPARATUS

BACKGROUND OF THE INVENTION

1) Field of the Invention

The present invention relates to an X-ray analyzing apparatus, and particularly to an apparatus arranged such that an X-ray detector and a cooling means for cooling the detector are sealed in a vacuum container and the characteristic X-ray generated from a sample to be analyzed is detected through an X-ray transmitting window provided on the vacuum container.

2) Related Art

FIG. 1 is a schematic view showing construction of a conventional X-ray analyzing apparatus. As shown in FIG. 1, the conventional X-ray analyzing apparatus comprises an excitation ray generator 11, a sample chamber 13 for containing a sample 12 and an X-ray detector 15 which is sealed in a vacuum container 14. A primary ray 16 which is generated from the excitation ray generator 11 is applied onto the sample 12 to allow that a characteristic X-ray 17 is generated from the sample. The generated characteristic X-ray 17 is then detected by the X-ray detector 15. The signal detected by the X-ray detector 15 is converted into an electric signal to conduct a qualitative/quantitative analysis of the object substance contained in the sample.

As the excitation ray generator 11, an ion source, an electron-beam generator, an X-ray generator, or a radiation source is preferably used. As the X-ray detector 15, a Silicon semiconductor element is preferred. The semiconductor detector 15 is connected to a heat conducting rod 19 and cooled by a cooling means 18 via the rod 19.

Cooling the detector reduces thermal noise and improves the signal to noise ratio so that an analysis with a high accuracy can be realized. The cooling means 18 is preferably a container which includes a refrigerant, such as liquid nitrogen, or a freezing device. In order to cool the semiconductor detector 15 effectively, the detector 15 and the cooling means 18 are sealed in a vacuum container 14. To maintain the vacuum condition in the vacuum container 14 in which the semiconductor detector 15 is contained and to introduce the characteristic X-ray 17 generated from the sample 12 into the semiconductor detector 15, an extremely thin X-ray transmitting window 20, made of Beryllium or an organic film, is provided between the sample chamber 13 and the vacuum container 18. The characteristic X-ray generated from the sample 12 is detected via the window 20.

In case a light element having a small atomic number is analyzed in such an X-ray analyzing apparatus, the attenuation of X-ray through the X-ray path of the apparatus should be as small as possible because the X-ray to be analyzed is apt to be easily attenuated and the energy level of the X-ray is low. In order to avoid the attenuation of the X-ray, the sample chamber 13 is generally arranged as a vacuum.

However, when a highly liquid, or highly volatile or a biological sample having a high liquid-water content, is analyzed, the sample chamber 13 is not arranged to be vacuumed because doing so would cause evaporation of the sample. A diaphragm between the sample and the sample chamber has been suggested to prevent the evaporation. However, when the sample chamber is arranged to be vacuumed, it does not help to make the diaphragm thick. If a thick diaphragm wall is provided between the sample and the sample chamber, the characteristic X-ray is attenuated by the diaphragm itself. Further the cost of manufacturing the apparatus becomes high because the material for such diaphragm is very expensive.

It has been suggested to purge a gas in the sample chamber 13, which does not prevent the transmission of the X-ray and does not generate the other characteristic X-rays which disturb the analysis of the object substance. Gases having a small atomic number, such as Hydrogen and Helium, do not prevent the transmission of X-rays. The characteristic X-rays generated from these gases have only small energy. These gases therefore can be preferably used to purge the sample chamber because the analyzing result is not effected by the characteristic X-rays generated from the gases. Helium gas is able to be treated safely and easily so that it is particularly favorable as the gas for purging the sample chamber.

In this manner, by purging the sample chamber 13 with a gas such as Helium, attenuation of the characteristic X-ray to be detected can be prevented in the sample chamber and high measurement accuracy can be retained, while the sample can be protected from evaporation. However, the conventional apparatus shown in FIG. 1 still has a drawback in that the gas purged into the sample chamber 13 leaks into the vacuum container 14. Leakage occurs because the apparatus is arranged such that the gas is directly contacted with the X-ray transmitting window 20 (a film made of Beryllium) by which the vacuum container 14 is separated from the sample chamber 13 and because Hydrogen or Helium is composed of such small molecules that they can pass through the lattice of the Beryllium atom. When the gas comes into the vacuum container 14, the vacuum condition of the vacuum container 14 deteriorates so that the heat insulating effect for the semiconductor X-ray detector 15 is gradually loosened. That is to say, the vacuum condition in the vacuum container 14 is deteriorated by the gas purging which should be done to protect the sample from evaporation. As a result, the consuming amount of two liquid nitrogen for cooling the semiconductor X-ray detector 15 increases in accordance with the deterioration of the vacuum condition of the vacuum container 14. If the consuming amount of utility such as the liquid nitrogen is increased, the liquid nitrogen supply period becomes quicker, leading to various problems would be caused such that the running cost of the apparatus increases and prediction for the period for exchanging the utility becomes difficult.

Further, since high electric power is applied to the semiconductor X-ray detector 15, if the vacuum condition of the vacuum container 14 deteriorates, a discharge is generated in the container so that performance of the semiconductor detector 15 itself is aggregated and leading to the possibility that the detector 15 would be broken.

SUMMARY OF THE INVENTION

The present invention is directed to an X-ray analyzing apparatus which overcomes at least some of the above-mentioned problems and others and prevents gas leaks in the vacuum container in which an X-ray detector is contained and kept cool. The cooling effect is thus deteriorated due to the decrease of the vacuum condition.

In order to solve the problem, the X-ray analyzing apparatus according to the invention comprises (a) an excitation ray generating means for applying an excitation ray onto a sample, (b) a vacuum container, (c) an X-ray detector sealed in the vacuum container, (d) a cooling means for cooling the X-ray detector also sealed in the vacuum container, (e) an interior of a sample chamber where a gas exists in a path of a characteristic X-ray which is generated from the sample, (f) a first X-ray transmitting window provided on the interior so that said characteristic X-ray can travel therethrough to the X-ray detector, (g) a second X-ray transmitting window provided on the vacuum container to allow the characteristic X-ray generated from the sample to reach to the X-ray detector through the first and second X-ray transmitting windows, wherein both windows are separated from each other to a second X-ray passing layer therebetween, and wherein said second X-ray passing layer is arranged to be vacuumed.

In this manner, according to the invention, since X-ray transmitting windows are provided both on the interior of the sample chamber and the vacuum container to keep the characteristic X-ray's path and these windows are separated from each other to provide a space, i.e. the second X-ray transmitting layer therebetween, the first X-ray passing layer is not directly made to contact the vacuum container. Therefore, the gas existing in the first X-ray passing layer leaking in the vacuum container can be prevented. Further, since the second X-ray passing layer is arranged to be vacuumed, the differential pressure between both sides of the second X-ray transmitting window, which is provided on the vacuum container, can be reduced to a small amount. Thus, even if the gas existing in the first X-ray passing layer leaks into the second X-ray passing layer, by making the second X-ray passing layer vacuumed, it would be hard for the gas to leak into the vacuum container. Furthermore, the characteristic X-ray can arrive to the X-ray detector without being attenuated when it goes through the second X-ray passing layer. According to the construction of the device, the vacuum condition in the vacuum container can be kept to prevent the deterioration of the performance of the X-ray detector and the amount of the cooling medium can be reduced. Further, since the characteristic X-ray generated from the sample is not attenuated, a more accurate analysis can be expected.

It should be noted that the vacuum condition in the second X-ray passing layer may be kept by using a vacuum pump or by the arranging a second X-ray passing layer as a vacuum sealed chamber.

In the device, a vacuum pump is provided to keep the vacuum condition in the second X-ray passing layer or the second X-ray passing layer is sealed. If providing a vacuum pump, the cost of manufacturing the apparatus becomes high. When the apparatus is applied to a process X-ray analyzer, the second X-ray passing layer is to be intermittently exhausted of gas to keep the vacuum condition so that the cost to operate the apparatus becomes high and the vacuum pump has to be maintained.

If the second X-ray passing layer is sealed to keep it vacuumed, the gas, such as Helium gas, which leaks into the second X-ray passing layer and stays in the vicinity of the second X-ray transmitting window provided on the vacuum container, leaks into the vacuum container in a certain amount so that the vacuum condition in the container deteriorates. To solve these problems, the X-ray analyzing apparatus according to an aspect of the invention comprises (a) an excitation ray generating means for generating an excitation ray and irradiating the excitation ray to a sample, (b) a vacuum container, (c) an X-ray detector sealed in the vacuum container, (d) a cooling means for cooling the X-ray detector also sealed in said vacuum container, (e) an interior of a sample chamber where a gas exists provided in a path of a characteristic X-ray which is generated from the sample and introduced into the X-ray detector, (f) a first X-ray transmitting window provided on the interior so that the characteristic X-ray generated from the sample passes through the first X-ray transmitting window, (g) a second X-ray transmitting window provided on the vacuum container so that the characteristic X-ray generated from the sample passes through the second X-ray transmitting window, both windows being separated from each other. A second X-ray passing layer is provided between the first and second windows and a second gas flows through the second X-ray passing layer.

According to the construction of the second aspect of the invention, even if the first gas existing in the first X-ray passing layer leaks into the second X-ray passing layer, the gas does not leak into the vacuum container in which the X-ray detector and the cooling device are sealed. Because the second gas is circulated in the second X-ray passing layer and then the first gas leaked in the second X-ray passing layer is flown out, it is thus possible to completely prevent deterioration of the vacuum condition in the vacuum container by the leakage of the first gas existing in the first X-ray passing layer into the vacuum container.

As the first gas, Hydrogen or Helium gas is preferably used. These elements do not prevent the transmission of X-ray. In addition, an energy of the characteristic X-ray generated from these element is so low, that even if such a gas exist in the first X-ray passing layer, it does not affect the analyzing result of the object substance.

As the second gas, atmospheric gas or nitrogen gas is preferably used. Since the size of molecules of these gases are larger than the size of the lattice of Beryllium atoms, they cannot pass through the lattice of the Beryllium, which is used as the material for the X-ray transmitting windows. Thus, when the second gas is introduced into the second X-ray passing layer, it does not leak into the vacuum container. Further, the effect which the gas gives to the analyzing result is very small. Particularly, nitrogen can be most preferably used because it does not react with the other substance.

It should be noted that the thinner the thickness of the second X-ray passing layer, the better the result. And it affects less the analyzing accuracy in the terms of absorption by the X-ray by the gas layer existing in the second X-ray passing layer, a reduction of a solid angle, a portion where the characteristic X-ray is generated (from the sample) viewed from the X-ray detector, and an existence of the characteristic X-ray generated from the substance included in the second gas in the second X-ray passing layer.

The X-ray analyzing apparatus according the second aspect of the invention may be modified in such a manner that liquid nitrogen is used as the refrigerant used for cooling the X-ray detector and nitrogen gas evaporated from the liquid nitrogen is used as the second gas.

As mentioned above, nitrogen gas is considered the best for the second gas which is introduced into the second X-ray passing layer because of its properties. If nitrogen gas is used as the second gas, the gas evaporated from the liquid nitrogen, which is used as a refrigerant used for cooling the semiconductor detector, is preferable. In this case, it becomes unnecessary to provide any means for introducing a gas into the second X-ray passing layer so that a simpler construction of the apparatus can be realized.

DETAILED DESCRIPTION OF THE PREFERRED EMBODIMENTS

The preferred embodiments will be explained below, with reference to the attached drawings.

Figure 2:
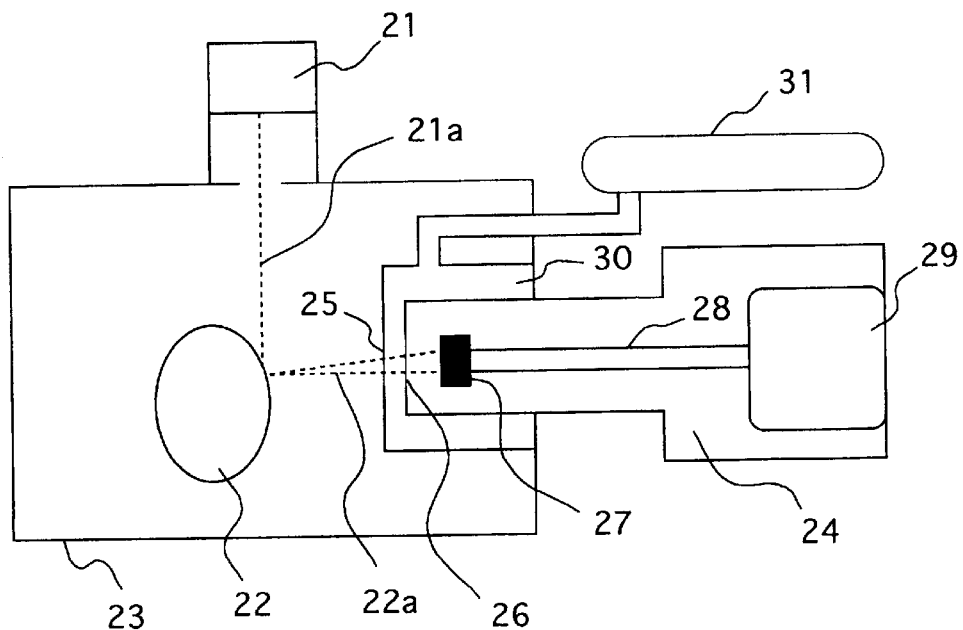
FIG. 2 is a schematic view depicting construction of an embodiment of the X-ray analyzing apparatus according to a first aspect of the invention.

FIG. 2 is a schematic view showing construction of the first embodiment of the X-ray analyzing apparatus according to the present invention. In FIG. 2, the numerical reference 21 represents an X-ray generator as an excitation ray generating means; 22 is a sample; 23 is a sample chamber for holding the sample 22 and being the path of the characteristic X-ray generated from the sample 22 when an excitation ray is applied thereon; 24 is a vacuum container; 25 is a first X-ray transmitting window provided on the sample chamber side; 26 is a second X-ray transmitting window provided on the vacuum container side; 27 is a semiconductor detector, 28 is a heat transferring rod; 29 a cooling device; 30 is a separation chamber (a second X-ray passing layer) provided between the first X-ray transmitting window 25 and the second X-ray transmitting window 26; and 31 designates a vacuum pump for exhausting the separation chamber 30 of gas.

In the apparatus shown in FIG. 2, the sample 22 which is an object to be analyzed is held in the sample chamber 23. The sample chamber 23 is purged with a gas, such as atmospheric gas, Helium or Hydrogen to secure a path for the characteristic X-ray generated from the sample 22. The excitation X-ray 21a generated from the X-ray generator 21 is applied onto the sample 22. The characteristic X-ray 22a generated from the sample 22 is made incident upon the semiconductor detector 27 transmitting through the first and second X-ray transmitting windows 25 and 26. The semiconductor detector 27 converts the applied X-ray into an electric signal to conduct a qualitative/quantitative analysis. The semiconductor detector 27 is connected to kept cool by the cooling means 29 using liquid nitrogen as a refrigerant. The heat transferring rod 28 and on the vacuum container 24 is provided the second X-ray transmitting window 26 to face the first X-ray transmitting window 25 which is provided on the sample chamber. The X-ray detector 27 and the heat transferring rod 28 and the cooling means 29 are sealed in the vacuum container 24 retaining its vacuum condition.

The chamber 30 separates the sample chamber 23 and the vacuum container 24 from each other. The first X-ray transmitting window 25 is provided on the path of the characteristic X-ray generated from the sample 22. The vacuum pump 31 is provided to exhaust the separation chamber 30 of gas to keep the vacuum condition there. That is, according to the first invention, the pressure difference on both sides of the second X-ray transmitting window 26 provided at the vacuum chamber side is reduced to a small amount by keeping the separation chamber 30 vacuum.

The characteristic X-ray 22a generated from the sample 22 passes through the two windows, i.e. the first X-ray transmitting window 25 at the sample chamber side of the separation chamber 30 and the second X-ray transmitting window 26 at the vacuum container side, and is detected by the semiconductor detector. Since the separation chamber 30 is kept in a vacuum condition by the vacuum pump 31, the differential pressure at both sides of the second X-ray transmitting window 26 can be reduced to a small amount. Thus the leaking of gas purged in the sample chamber 23 into the vacuum container 24 can be prevented. Further, since the separation chamber 30 is kept in a vacuum condition, the characteristic X-ray 22a can arrive to the semiconductor detector 27 without being attenuated.

In this manner, since the pressure difference at both sides of the second X-ray transmitting window 26 is reduced to a small amount and the sample chamber 23 and the vacuum container 24 are separated from each other by X-ray transmitting windows 25 and 26, the second X-ray transmitting window 26 does not make contact directly to the gas which purges the sample chamber 23. It can be prevented that gas leaks into the vacuum container 24 and the cooling effect of the semiconductor detector 27 deteriorates because the vacuum condition of the vacuum container decreases.

In the above-mentioned embodiment, the vacuum condition in the separation chamber 30 may be obtained by exhausting the chamber of gas with the aid of the vacuum pump. However, it may be possible to arrange the separation chamber 30 to be sealed in a vacuum condition.

Figure 3:
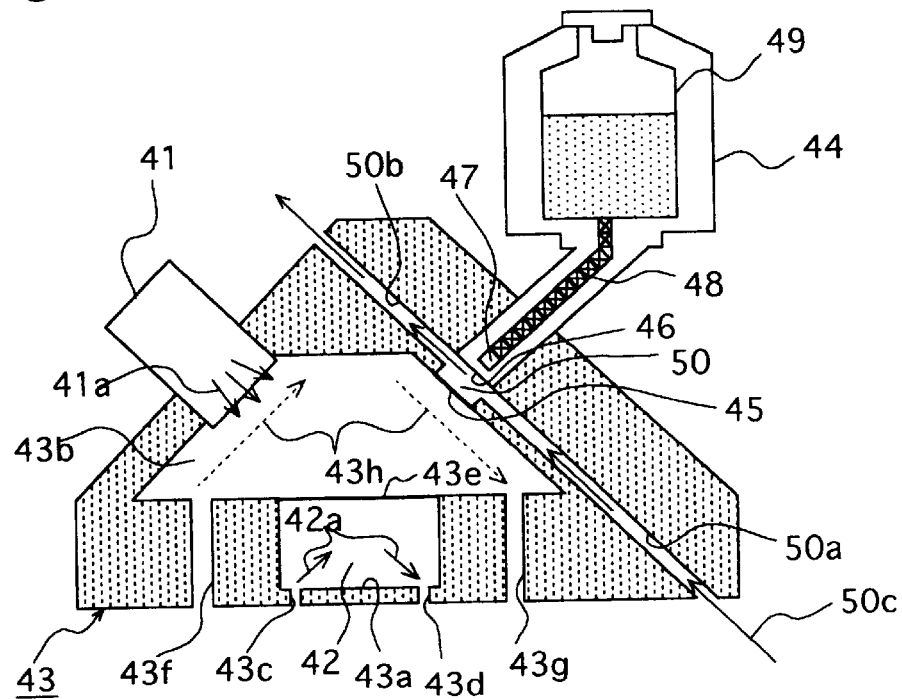
FIG. 3 is a schematic view illustrating construction of an embodiment of the X-ray analyzing apparatus according to a second aspect of the invention.

FIG. 3 is a schematic view depicting the second embodiment according to the second aspect of the present invention. The numerical reference 41 represents an X-ray generator as an excitation ray generating means; 42 is a sample, 43 is a sample chamber being a path (the first X-ray passing layer) for the characteristic X-ray, which is generated from the sample 42 when the excitation ray is applied thereon; 44 is a vacuum container; 45 is a first X-ray transmitting window provided on the sample chamber side; 46 is a second X-ray transmitting window provided on the vacuum container side; 47 is a semiconductor detector; 48 is a heat transferring rod, 49 is a cooling means; and 50 designates a space with the second X-ray passing layer provided between the first and second X-ray transmitting windows 45 and 46. It should be noted that a liquid sample is measured in this and the following embodiments.

The sample chamber 43 comprises a flow cell 43a by which liquid sample 42 is introduced to the area where an excitation X-ray 41a generated from the X-ray generator 41 is applied and an X-ray path chamber 43b in which a path for the characteristic X-ray, which is generated when the excitation X-ray is applied onto the sample 42, is secured. There are provided an inlet 43c and an outlet 43d in the flow cell 43a so that the liquid sample 42 flows in the direction shown by an arrow 42a. A thin film 43e made of Beryllium is provided between the flow cell 43a and the X-ray path chamber 43b to prevent the evaporation of the liquid sample 42. In the X-ray path chamber 43b, there also are provided an inlet 43f and an outlet 43g, through which Hydrogen gas or Helium gas is supplied to purge the X-ray path chamber 43b.

The semiconductor detector 47 is cooled by the cooling device 49 via the thermal conducting rod 48 to reduce the signal to noise ratio. The semiconductor detector 47, the thermal conducting rod 48 and the cooling device 49 are sealed in the vacuum container 44 keeping its vacuum condition to interrupt a thermal effect from the outside. There are provided the first X-ray transmitting window 45 made of Beryllium in the path for the characteristic X-ray in the X-ray path chamber 43b of the sample chamber 43 and the second X-ray transmitting window 46, which is also made of Beryllium, which is in the X-ray path formed at the vacuum container 44 side. These windows are separated from each other to form a space with the second X-ray passing layer between them. There are provided an inlet 50a and an outlet 50b so that air can be circulated through the space 50 in the direction shown by arrow 50c.

In FIG. 3, the excitation X-ray 41a generated from the X-ray generator 41 is applied onto the liquid sample 42. The characteristic X-ray (fluorescent X-ray) is then generated from the object substance contained in the liquid sample 42 and is introduced to the semiconductor detector 47 through the first X-ray transmitting window 45 provided on the X-ray passing chamber 43b side and the second X-ray transmitting window 46 arranged on the vacuum container 44 side. The signal detected by the semiconductor detector 47 is then converted into an electric signal to conduct a qualitative/quantitative analysis.

Since the gas purged in the X-ray passing chamber 43, i.e. Hydrogen gas or Helium gas, has small molecules, the gas passes through the first window 45, which is made of Beryllium, and then leaks into the space 50 provided between the first window 45 on the X-ray passing chamber 43b side and the second window 46 on the vacuum container 44 side. However, in this embodiment, since air is circulated in the space 50, the Hydrogen or Helium molecules leaked into the space 50 are discharged to the outside via the outlet 50b along with the circulated air, so that the Hydrogen molecules or the Helium molecules do not leak into the vacuum container 44. That is to say, according to the apparatus of the present embodiment, the Hydrogen molecules or the Helium molecules for purging the X-ray passing chamber 43b leak into the space 50, but do not stay in the vicinity of the second X-ray transmitting window 46 and do not leak into the space 50. A deterioration of the vacuum container 44 due to the leakage of the purging gas can therefore be prevented.

It should be noted that air having a low dew point and including no dust should be circulated in space 50. For this purpose, instrumentation grade air is preferable. Further, the density of the air to be circulated through the space and the circulating speed should be settled so as not to apply any exceeding pressure to the thin Beryllium film used for the first and second X-ray transmitting windows 45 and 46 because these films have only a low withstanding pressure.

Figure 4:
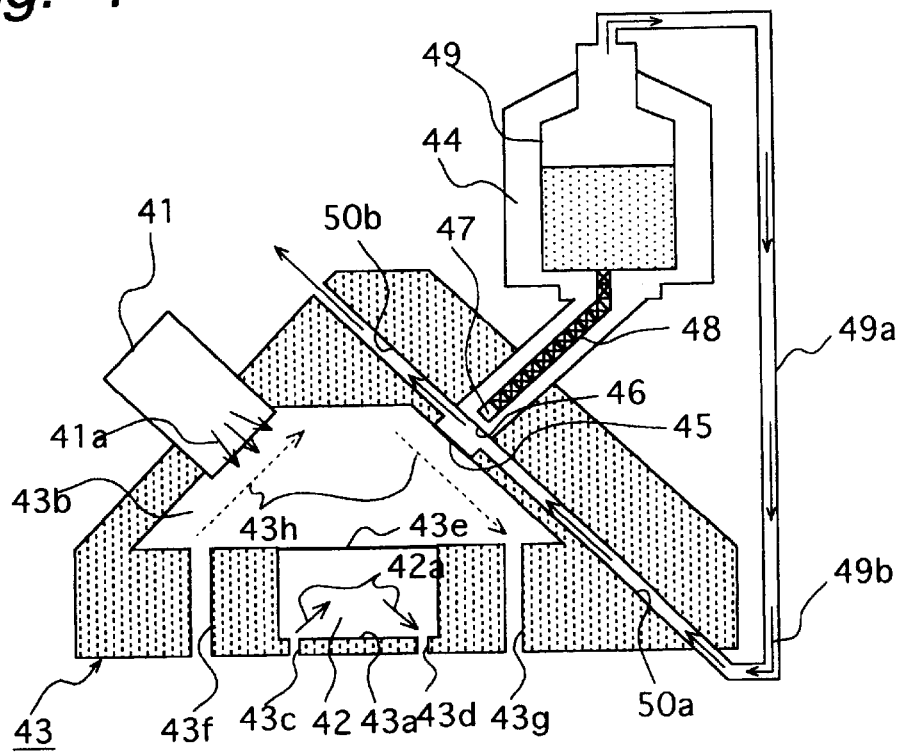
FIG. 4 is a schematic view representing another embodiment of the X-ray analyzing apparatus according to the second aspect of the invention.

FIG. 4 is a schematic view illustrating a construction of the modified embodiment of the second aspect of the present invention. In this embodiment, the apparatus is arranged such that nitrogen gas is circulated in the space 50 provided between the first X-ray transmitting window 45 and the second X-ray transmitting window 46. It should be noted, the same numerical numbers are used for the same elements as those which are mentioned in the second embodiment shown in FIG. 3 and the explanation therefor is omitted here.

In the second embodiment shown in FIG. 3, air is circulated through the space 50. However, the air includes not only oxygen and nitrogen but also various other substances. These substances sometime influence the measurement accuracy of the object substance to be analyzed when the characteristic X-ray generated from the substances contained in the air has a level which is close to that of the characteristic X-ray generated from the object substance to be analyzed. For instance, the level of the characteristic X-ray generated from argon, which is contained in the air, is 2.96 Kev. The level is close to that of the characteristic X-ray of sulfur, which is 2.31 Kev. Therefore, if the object substance to be analyzed is sulfur, the spectrum of sulfur is superimposed onto that of argon so that there remains a possibility that the measurement result is influenced by the existence of argon in the circulated air.

By contrast, nitrogen and oxygen have large molecules so that they cannot pass through the lattice of Beryllium atoms of the second X-ray transmitting window 46 on the vacuum container 44 side. Further, since the energy level of the characteristic X-ray of these elements is small, the characteristic X-ray generated from nitrogen or oxygen does not exert so much influence to the measurement accuracy of the sulfur. For these reasons, nitrogen or oxygen can be preferably used for the gas to be circulated in space 50.

In the embodiment shown in FIG. 4, the inlet 50a of the space 50 is connected to a liquid nitrogen tank 49 for use in cooling the semiconductor detector 47 by duct 49a, so that evaporated gas of the liquid nitrogen is taken into the space 50 as the gas to be circulated there. According to this construction, only by a simple construction, i.e. connecting the inlet 50a of the space 50 to the liquid nitrogen tank 49, the nitrogen gas evaporated from the tank is naturally introduced into the space 50 as shown by an arrow 49b then exits from the outlet 50b. It is therefore not necessary to provide any cylindered nitrogen gas to introduce nitrogen gas into space 50, so that the second invention can be realized with a simple construction. In this manner, according to the modified embodiment shown in FIG. 4, the nitrogen gas evaporated from the liquid nitrogen for use in cooling the semiconductor detector can be effectively used to be circulated through space 50. The number of parts constituting the apparatus can then be reduced.

Figure 1:
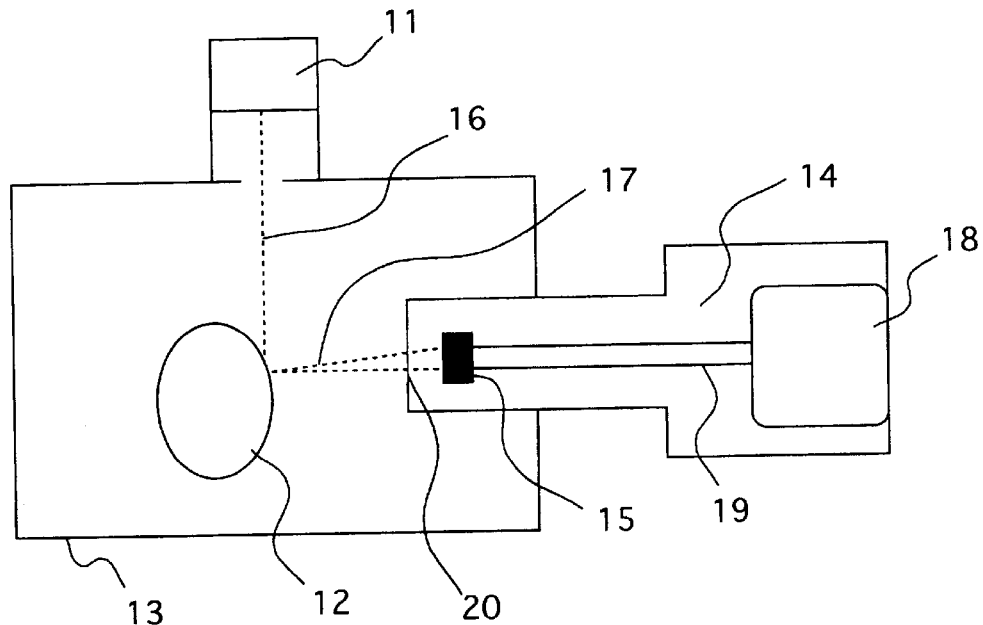
FIG. 1 is a schematic view showing construction of a conventional X-ray analyzing apparatus.
Figure 5:
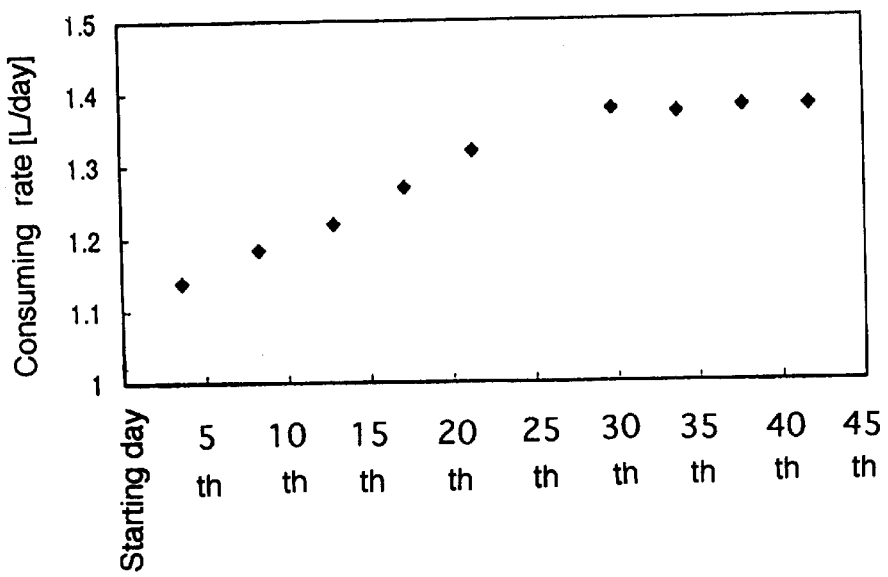
FIG. 5 is a graph showing an improvement of the effect of the consuming rate of liquid nitrogen in case the second aspect of the invention is applied to the apparatus.

FIG. 5 is a graph showing an effect of the improvement of the consumption rate of the liquid nitrogen for use in cooling the semiconductor detector in the X-ray analyzing apparatus according to the second invention. From the starting day of the experiment to the 20th day, the conventional X-ray analyzing apparatus shown in FIG. 1 is operated and, after the 30th day, the X-ray analyzing apparatus according to the second invention is operated instead of the conventional apparatus in order to recognize the change of the consumption rate of the liquid nitrogen. As shown in the graph in FIG. 5, from the starting day until the 20th day, the consumption rate of the liquid nitrogen was not constant. This means the consumption rate increased as days go by. By contrast, after the 30th day, the apparatus according to the second invention is started to be used, the consumption rate of the liquid nitrogen becomes constant, i.e. 1.4 litter per day. It can apparently be understood from the experiment that the deterioration of the vacuum condition of the vacuum container 44 is improved after the apparatus according to the invention was started to be used.

The graph in FIG. 5 shows an example of the measurement result of the consumption rate of the liquid nitrogen where the conventional X-ray analyzing apparatus was first used for 20 days and then the apparatus according to the invention takes the place of the conventional one after the vacuum condition in the vacuum container has been deteriorated. In case the apparatus according to the invention was used from the starting day, i.e. before the vacuum condition deteriorated, the consumption rate of the liquid nitrogen was constant from the first, i.e. about 1 liter per day.

As clear from the above experiment, the deterioration of the vacuum condition in the vacuum container can be improved so that the consumption rate of the liquid state nitrogen can be kept constant. It thus becomes easier to predict the exchange timing of the nitrogen bomb and to calculate the running cost of the apparatus.

However, if space 50 is provided between the sample chamber 43 and the vacuum container 44 and air layer or nitrogen layer exists in the space 50, there would be concern as the measurement accuracy of the apparatus would be decreased to some degree in comparison to the conventional apparatus where no space is provided. The reasons for such a concern are:

(1) the characteristic X-ray generated from the sample 42 is absorbed by the gas layer in the space 50;

(2) since the distance between the sample 42 and the detector 47 becomes longer in comparison to the conventional apparatus and then the solid angle at the portion where the characteristic X-ray is generated, viewed from the detector 47 becomes small so that the number of X-ray which arrives to the detector is decreased; and (3) if air is circulated in space 50, the measurement of the object substance is influenced by the characteristic X-ray generated from some substance contained in the air because the level of the characteristic X-ray generated from the substance contained in the air is close to that of the object substance contained in the sample.

Figure 6:
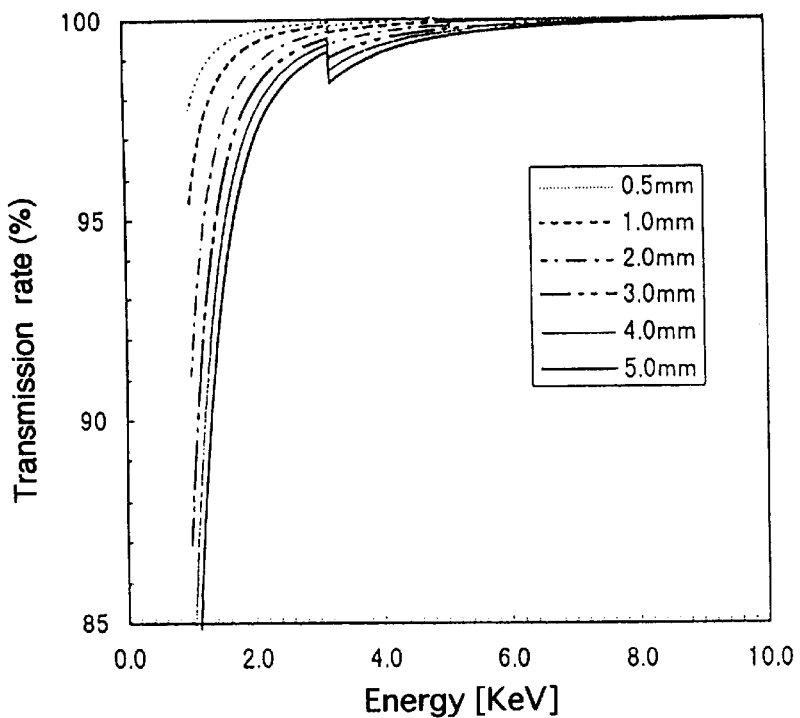
FIG. 6 is a graph depicting transmitting rate of X-ray when an air layer is provided between the sample chamber and the vacuum container.

However, the below-mentioned study demonstrates that these concerns are unwarranted or can be solved by certain countermeasures:

The inventors studied about the first and second concerns mentioned above. FIG. 6 is a graph depicting X-ray transmission ratios when an X-ray passes through air layers having their thickness of 1.0 mm, 2.0 mm, 3.0 mm, 4.0 mm, and 5.0 mm, respectively. FIG. 6 demonstrates that the thicker the space, the lower the X-ray transmission ratio because the X-ray is absorbed by the air.

However, the inventors conducted an experiment in which the space 50 is arranged to have its thickness of 3.0 mm. An X-ray was applied through the space. An influence by the X-ray absorption due to the air layer (the first concern) and by the decrease of solid angle (the second concern) are then searched. As a result, the decrease of the number of X-ray photons is only about 10%. Such a decrease of the number of X-ray photons could be compensated for by increasing the tube current of the X-ray tube 41 and strengthening the intensity of X-ray generated therefrom. It was therefore proved that the above-mentioned first and second concerns could be solved by the countermeasures.

Figure 7:
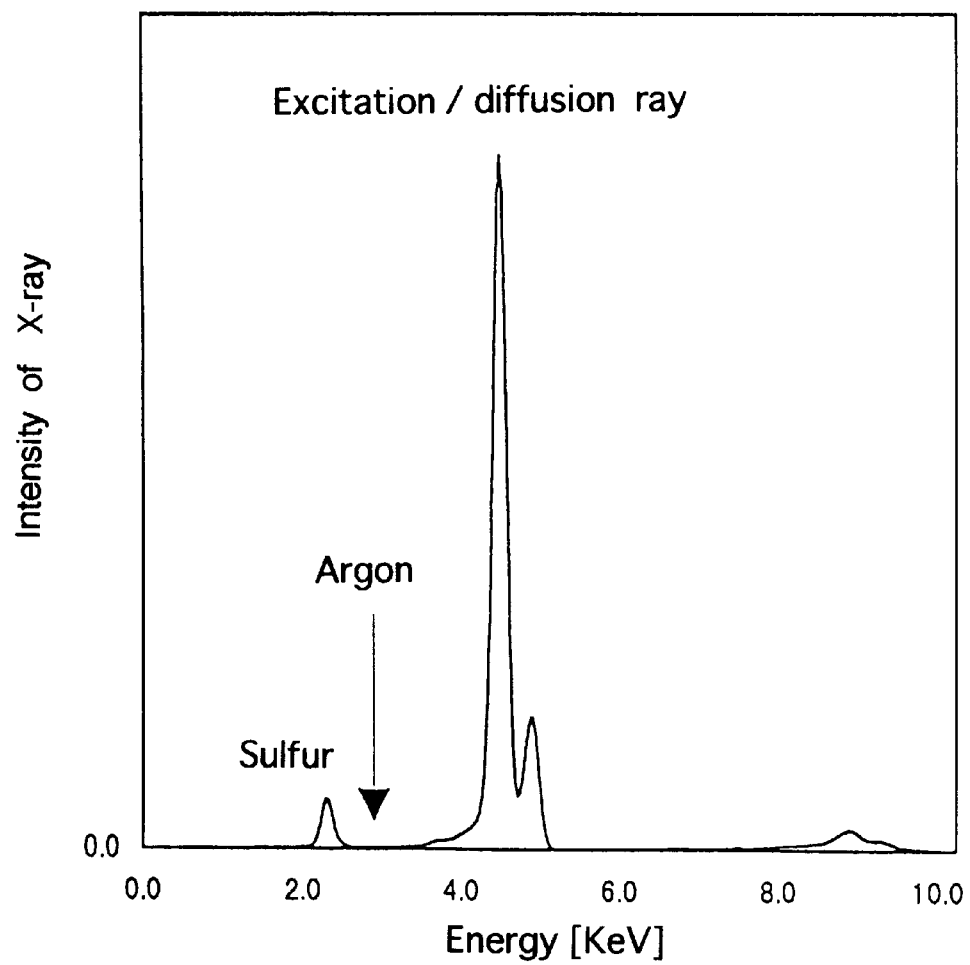
FIG. 7 is a graph illustrating an example of X-ray spectrum detected from a high sensitivity process sulfur detecting apparatus.

The inventors further studied about the third concern. For instance, when sulfur component is an object to be measured, and if an air is introduced in the space 50, the spectacle of the characteristic X-ray of sulfur is superimposed to that of argon contained in the air. Thus, it is feared the measurement result is influenced by the existence of argon because the energy level of both characteristic X-rays of sulfur and argon are close each other. However, experimental results show that the amount of argon contained in the air was very little. Thus no characteristic X-ray of argon which interferes with the measurement for sulfur component was found, as shown in FIG. 7. It should be noted that the experiment was conducted under the condition that the X-ray analyzing apparatus having a space 50 with its thickness of 3 mm was applied to a sulfur measurement apparatus. Should there be concern that some components contained in the air, such as argon, affects the measurement result of the object substance, nitrogen gas or oxygen gas can be used to be circulated through the space 50 instead of air.

Figure 8:
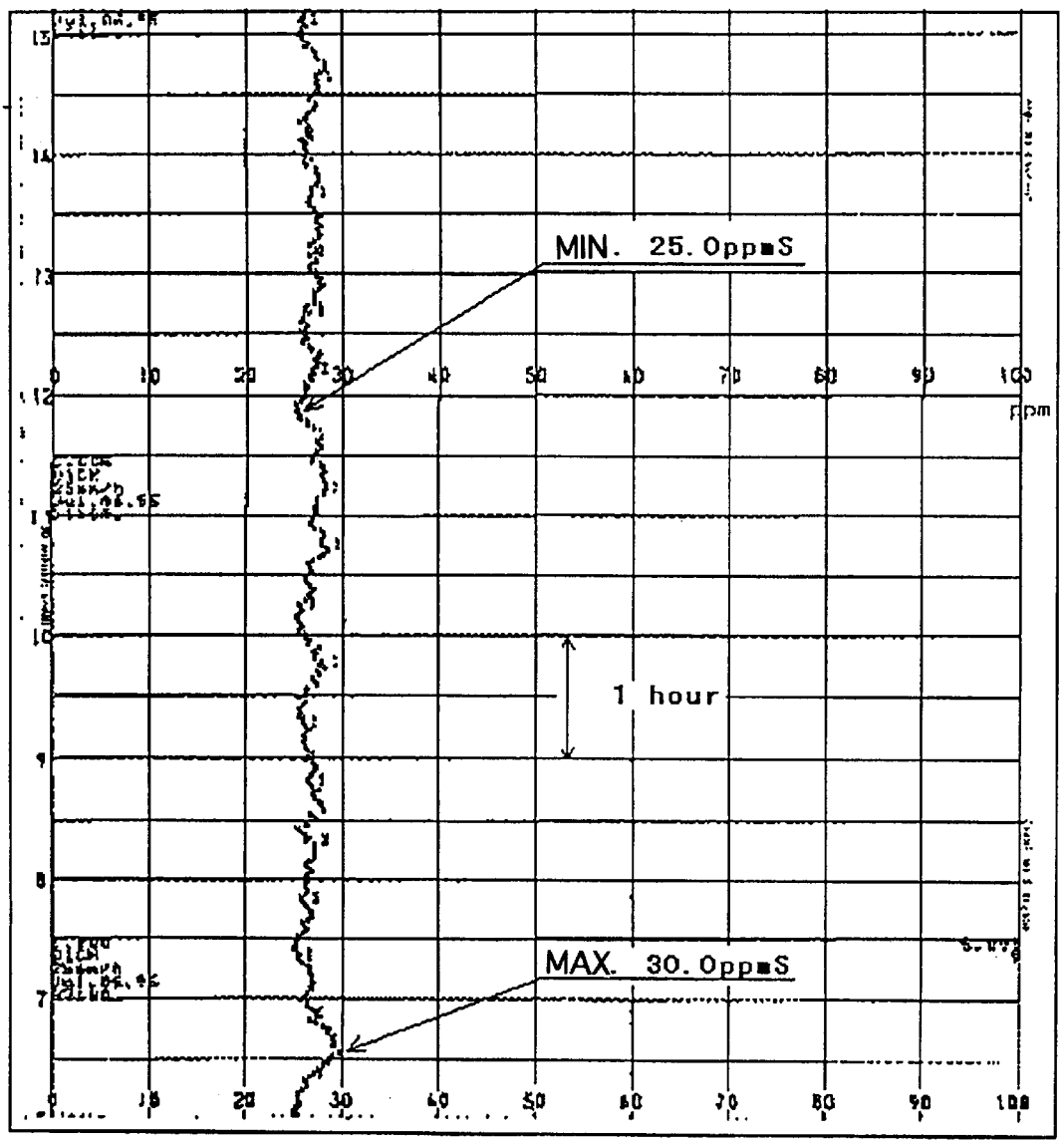
FIG. 8 is a graph representing a measurement chart of sulfur concentration which is measured by using an X-ray analyzing apparatus according to the second aspect of the invention.

On the other hand, the inventors applied the X-ray analyzing apparatus according to the invention to a process sulfur detector to evaluate its sulfur detecting performance with a reproduction of the measurement values. FIG. 8 is a chart representing an example of a measurement result of sulfur concentration which is measured by the process sulfur detector to which the present invention is applied. In the apparatus, a sample containing sulfur, whose concentration has been known, is circulated in the sample chamber. It is clear from the chart shown in FIG. 8 that the measurement of sulfur was conducted in stable condition for 8 hours or more. In the chart shown in FIG. 8, the maximum measurement value is 30 ppmS, and the minimum measurement value is 25.0 ppmS. When the difference between the maximum value and the minimum value is $\pm 3\sigma$ and the standard deviation is obtained by dividing the difference by six, the standard deviation $1\sigma$ becomes 0.83 ppmS ($1\sigma$=0.83 ppmS). This bears in comparison with the standard deviation $1\sigma$ when no space (second X-ray passing layer) is provided, which is 0.76 ppmS.

As is clear from the above explanation, according to the first aspect of the invention, since the X-ray transmitting window disposed in front of the X-ray detector is not directly made to contact to the gas which purges the sample chamber, i.e. helium or hydrogen, the purging gas leaks into the vacuum container where the X-ray detector is sealed is prevented. Further, even though the purging gas passes through the X-ray transmitting window, the amount of the gas can be reduced to only a small amount, i.e. at least to 3 units fewer, because the pressure difference on both sides of the X-ray transmitting window provided at the vacuum container side is made small. As a result, the deterioration of the cooling effect of the semiconductor detector due to the decrease of the vacuum condition can be prevented. Then, the life time of the X-ray detector can be prolonged for a considerably long time; further the consumption amount of the refrigerant, i.e. liquid nitrogen, can be reduced.

Further, according to the X-ray analyzing apparatus of the second aspect of the invention, a space (the second X-ray passing layer) is provided between the sample chamber and the vacuum container and gas is circulated in the space. Therefore, even if the gas purged in the sample chamber leaks into the space, the gas does not stay in the vicinity of the second X-ray transmitting window provided on the vacuum container, so that the deterioration of the vacuum condition in the vacuum container can be prevented more easily. As a result, the consumption rate of the liquid nitrogen for use in cooling the semiconductor detector can be kept constant and then the exchange timing of the nitrogen bomb can be established easily and the running cost of the apparatus can be calculated without any difficulty, which means that the maintenance for the apparatus as a whole becomes very easy.

While the preferred and alternate embodiments of the invention has been depicted in detail, modification and adaptations have been made thereto without departing from the spirit and scope of the invention as delineated in the following claims.

What is claimed is:

1. An X-ray analyzing apparatus which comprises an excitation ray generating means for applying an excitation ray onto a sample, a vacuum container, an X-ray detector sealed in said vacuum container, a cooling means for cooling said X-ray detector being also sealed in said vacuum container, and an interior of a sample chamber being purged with a gas being located in a path of X-ray from said sample to said X-ray detector through which a characteristic X-ray generated from said sample passes; comprising a first X-ray transmission window being provided on said interior and a second X-ray transmission window being provided on said vacuum container so that said characteristic X-ray generated from the sample travels through these windows, wherein the first and second X-ray transmission windows are separated from each other so as to provide an X-ray passing layer therebetween; and wherein said X-ray passing layer is arranged to be vacuumed.

2. An X-ray analyzing apparatus according to claim 1, said apparatus further comprising a pumping means for exhausting an air through said X-ray passing layer so as to make the layer vacuumed; and wherein said X-ray passing layer is arranged to be vacuumed by means of said pumping means.

3. An X-ray analyzing apparatus according to claim 1, wherein said X-ray passing layer is arranged as a vacuum sealed chamber.

4. An X-ray analyzing apparatus according to anyone of claims 1 to 3, wherein said gas existing in said interior of said sample chamber is Helium gas or Hydrogen gas.

5. An X-ray analyzing apparatus which comprises an excitation ray generating means for applying an excitation ray onto a sample, a vacuum container, an X-ray detector sealed in said vacuum container, a cooling means for cooling said X-ray detector being also sealed in said vacuum container, and an interior of a sample chamber being purged with a gas being located in a path of X-ray from said sample to said X-ray detector through which a characteristic X-ray generated from said sample passes; comprising a first X-ray transmission window being provided on said interior and a second X-ray transmission window being provided on said vacuum container so that said characteristic X-ray generated from the sample travels through these windows, wherein the first and second X-ray transmission windows are separated from each other so as to provide an X-ray passing layer therebetween; and wherein a second gas, which is different from said first gas, is circulated through said X-ray passing layer.

6. An X-ray analyzing apparatus according to claims 5, wherein said first gas existing in said interior of said sample chamber is Helium gas or Hydrogen gas.

7. An X-ray analyzing apparatus according to claim 6, wherein said second gas circulated thorough said X-ray passing layer has its molecular weight heavier than that of said first gas existing in said interior of said sample chamber.

8. An X-ray analyzing apparatus according to claim 6, wherein said second gas circulated through said X-ray passing layer is an atmospheric gas or Nitrogen gas.

9. An X-ray analyzing apparatus according to anyone of claims 5 to 8, wherein liquid nitrogen is used as a refrigerant for use in said cooling means for cooling said X-ray detector, and wherein Nitrogen gas evaporated from said liquid nitrogen used as the refrigerant is used for said second gas.

* * * * *